United States Patent
Yamamura et al.

[11] Patent Number: 6,027,628
[45] Date of Patent: Feb. 22, 2000

[54] GEL CASSETTE FOR ELECTROPHORESIS

[76] Inventors: Hidetaka Yamamura, 83-17 Matsubara, Matsumoto City, Nagano Prefecture, Japan, 399; Richard T. L. Chan, 1515 Crespo Dr., La Jolla, Calif. 92037

[21] Appl. No.: 09/028,180

[22] Filed: Feb. 23, 1998

[51] Int. Cl.[7] .................. G01N 27/26; G01K 27/447
[52] U.S. Cl. .................. 204/618; 204/461; 204/466; 204/467; 204/612; 204/616
[58] Field of Search ............... 204/456, 457, 204/458, 459, 461, 462, 463, 464, 465, 466, 467, 468, 469, 470, 605, 607, 608, 609, 610, 612, 613, 614, 615, 616, 617, 618, 619, 620, 621

[56] References Cited

U.S. PATENT DOCUMENTS

| | | | |
|---|---|---|---|
| 3,129,158 | 4/1964 | Raymond et al. | 204/467 |
| 3,442,686 | 5/1969 | Jones | 428/336 |
| 3,932,263 | 1/1976 | Brefka | 204/617 |
| 4,548,869 | 10/1985 | Ogawa et al. | 428/616 |
| 4,548,870 | 10/1985 | Ogawa et al. | 428/616 |
| 4,576,693 | 3/1986 | Kreisher et al. | 204/620 X |
| 4,579,783 | 4/1986 | Ogawa et al. | 428/475.2 X |
| 4,600,641 | 7/1986 | Ogawa et al. | 428/355 AC |
| 4,718,998 | 1/1988 | Ogawa et al. | 204/606 |
| 4,722,777 | 2/1988 | Ogawa et al. | 204/606 |
| 4,729,823 | 3/1988 | Guevara, Jr. | 204/621 |
| 4,737,258 | 4/1988 | Ogawa et al. | 204/606 |
| 4,737,259 | 4/1988 | Ogawa et al. | 204/606 |
| 4,762,743 | 8/1988 | von Alven et al. | 428/156 |
| 4,833,332 | 5/1989 | Robertson, Jr. et al. | 204/612 X |
| 4,834,854 | 5/1989 | Sugihara et al. | 204/470 |
| 4,844,786 | 7/1989 | Sugihara et al. | 204/616 |
| 4,897,306 | 1/1990 | Sugimoto et al. | 428/336 |
| 4,904,366 | 2/1990 | Tokita et al. | 204/461 |
| 4,954,236 | 9/1990 | Kushner et al. | 204/466 |
| 5,084,356 | 1/1992 | Deak et al. | 428/458 |
| 5,085,904 | 2/1992 | Deak et al. | 428/35.7 |
| 5,190,629 | 3/1993 | Sugihara et al. | 204/466 |
| 5,190,632 | 3/1993 | Fujimiya et al. | 204/612 X |
| 5,230,781 | 7/1993 | Middendorf et al. | 204/467 X |
| 5,498,475 | 3/1996 | Takigawa et al. | 428/334 |
| 5,685,967 | 11/1997 | Manis et al. | 204/616 |

OTHER PUBLICATIONS

Vitor M.C. Madeira et al "Bargain Electrophoresis" Journal of Chemical Education, vol. 63, No. 12, pp. 1109–111, Dec. 1986.

*Primary Examiner*—Jill Warden
*Assistant Examiner*—John S. Starsiak, Jr.
*Attorney, Agent, or Firm*—John L. Rogitz

[57] ABSTRACT

A gel cassette for electrophoresis includes opposed plastic plates holding a gel therebetween. An upper buffer tank can be adhered to one of the plates by double backed tape that is sandwiched between the tank and plate, thereby avoiding the use of a rubber sealing gasket between the tank and plate. As a result, the distance between the tank and the plate is kept constant. A buffer solution in the tank communicates with the gel. The cassette can then be placed in a lower buffer tank and an electric field applied to the buffer solutions to effect electrophoresis of DNA fragments that have been placed in the gel. In an alternate embodiment, a window is formed in one of the plastic plates to allow laser light to pass into the cassette and excite a fluorescent tag in the DNA. The fluorescence then passes back through the window for detection by a sensor, to automatically determine the DNA sequence of the sample in the gel in accordance with auto DNA sequencing principles. The window reduces and indeed eliminates absorption, interference, and/or reflection of the relatively weak fluorescent signal emitted by the DNA tag.

18 Claims, 3 Drawing Sheets

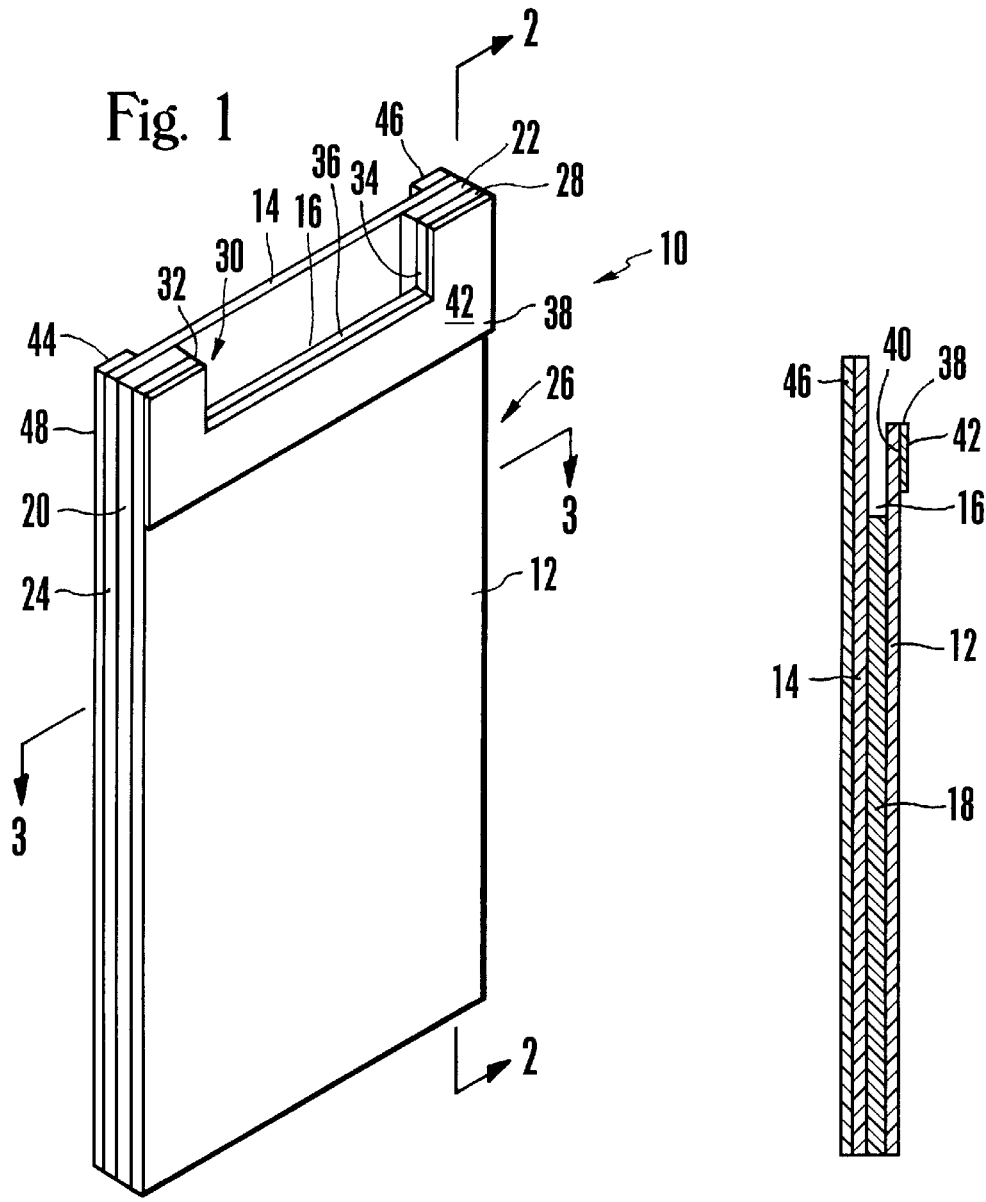
Fig. 1
Fig. 2
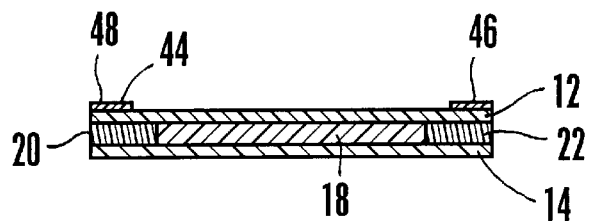
Fig. 3

GEL CASSETTE FOR ELECTROPHORESIS

FIELD OF THE INVENTION

The present invention relates generally to electrophoresis analysis, and more particularly to gel cassettes for electrophoretic DNA sequencing.

BACKGROUND

Electrophoresis is a process that can be used to analyze substances. An example of an electrophoretic analysis is DNA sequencing, which is a type of analysis undertaken to analyze the genetic sequence of a sample of DNA. In one type of electrophoretic DNA sequencing, a polyacrylamide gel is held between two plates of a so-called cassette, and the DNA sample to be analyzed is deposited on the gel. If desired, the DNA sample can be tagged with a radioisotope for manual electrophoresis sequencing or the DNA sample can be tagged with a fluorescent substance for automatic DNA sequencing. Then, the cassette is placed in or conveyed through an electrophoresis apparatus for exposing the gel to an electric field. Under the influence of the electric field, the various constituents in the DNA migrate through the gel at various rates depending on their sizes, thereby separating from each other and facilitating analysis of the sample.

In manual electrophoresis, the sample is removed from the electrophoresis apparatus and analyzed by, e.g., x-ray photoimagery of the radioisotope-tagged sample. On the other hand, in automatic electrophoresis the cassette is illuminated with light having a predetermined wavelength to cause the fluorescent tag of the DNA sample to emit fluorescence, which is then detected by a sensor in the electrophoresis apparatus and correlated to a genetic composition. Relatively expensive glass cassettes have heretofore been used in automatic electrophoresis that use principles of fluorescence, because such cassettes, when made of glass instead of plastic, advantageously minimize reflection and/or interference with the relatively weak fluorescence that is typically emitted by fluorescently-tagged DNA samples.

Both manual and automatic electrophoresis can be undertaken by orienting the cassette upright, or vertically, in the electrophoresis apparatus. In vertical electrophoresis, a portion of one of the cassette plates is cutout near the top of the plate, and an upper buffer tank is fastened to the cassette next to the cutout and filled with a buffer solution, such that the solution communicates with the gel in the gel chamber. The lower end of the cassette is then placed in a lower buffer solution and the electric field applied to the gel by means of the upper (cathodic) solution and lower (anodic) solution. To ensure that no buffer solution leaks from between the upper buffer tank and the cassette plate, the buffer tank is formed with a groove, and a resilient gasket is positioned in the groove to establish a seal between the plate and the tank.

As recognized by the present invention, present glass cassettes are both expensive and fragile. Consequently, they are easily broken during shipment from the cassette manufacturer to customer laboratories. The present invention additionally recognizes that the requirement to form the upper buffer tank with a groove for the sealing gasket further increases the cost of the cassette. As recognized herein, however, it is possible to provide an inexpensive yet effective cassette for vertical electrophoresis that can be used in existing electrophoresis apparatus and that nevertheless can be configured for minimizing interference with fluorescence emitted from a DNA sample.

Accordingly, it is an object of the present invention to provide an inexpensive gel cassette for electrophoresis that can be used in existing manual or automatic electrophoresis apparatus. Another object of the present invention is to provide a gel cassette for electrophoresis that does not require a gasket groove to be formed in an upper buffer tank. Still another object of the present invention is to provide a gel cassette for electrophoresis that is made of plastic and that is configured for minimizing interference with fluorescent light from a DNA sample tag. Yet another object of the present invention is to provide a gel cassette for electrophoresis that is easy to use and cost effective to manufacture.

SUMMARY OF THE INVENTION

A cassette for electrophoresis includes a first plate, a second plate facing the first plate, and a gel chamber between the plates. At least one adhesive element is adhesively attached to one of the plates, and the adhesive element defines an adhesive tank surface facing away from the plates for engaging an upper buffer tank when the upper buffer tank is pressed against the adhesive element.

In a preferred embodiment, the upper buffer tank defines a buffer chamber and the adhesive element is attached to the first plate. The first plate is formed with a cutout, and the adhesive element borders the cutout for holding the upper buffer tank against the first plate with the buffer chamber of the upper buffer tank in communication with the cutout. Preferably, the plates are made of plastic and the cassette further includes a gel disposed between the plates.

At least one glass adhesive element is attached to the second plate. The glass adhesive element defines an adhesive glass engaging surface facing away from the plates for holding a glass cover in juxtaposition with the second plate. This glass cover supports the plates during electrophoresis.

In an alternate embodiment, the gel chamber can hold at least one fluorescent constituent and the first plate is formed with a light passageway to permit light to propagate therethrough into the gel chamber and thereby cause the fluorescent constituent to emit fluorescence. A passageway cover is selectively engageable with the first plate to selectively block the light passageway.

In another aspect, a cassette for electrophoresis includes a first plate, a second plate facing the first plate, and a gel chamber therebetween. The gel chamber can hold a gel having at least one fluorescent constituent. At least the first plate or second plate is formed with a light passageway to permit light to propagate therethrough into the gel chamber and thereby cause the fluorescent constituent to emit fluorescence.

In still another aspect, a method for DNA sequencing includes holding a gel between two plastic plates, and attaching an upper buffer tank defining a buffer chamber to one of the plates using an adhesive tape having first and second adhesive sides. The method then includes disposing the plates in an electrophoresis apparatus for undertaking DNA sequencing.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of a first embodiment of the present cassette for manual DNA sequencing, with the upper buffer tank and glass cover removed;

FIG. 2 is a cross-sectional view as seen along the line 2—2 in FIG. 1;

FIG. 3 is a cross-sectional view as seen along the line 3—3 in FIG. 1;

DETAILED DESCRIPTION OF THE PREFERRED EMBODIMENT

Figure 4:
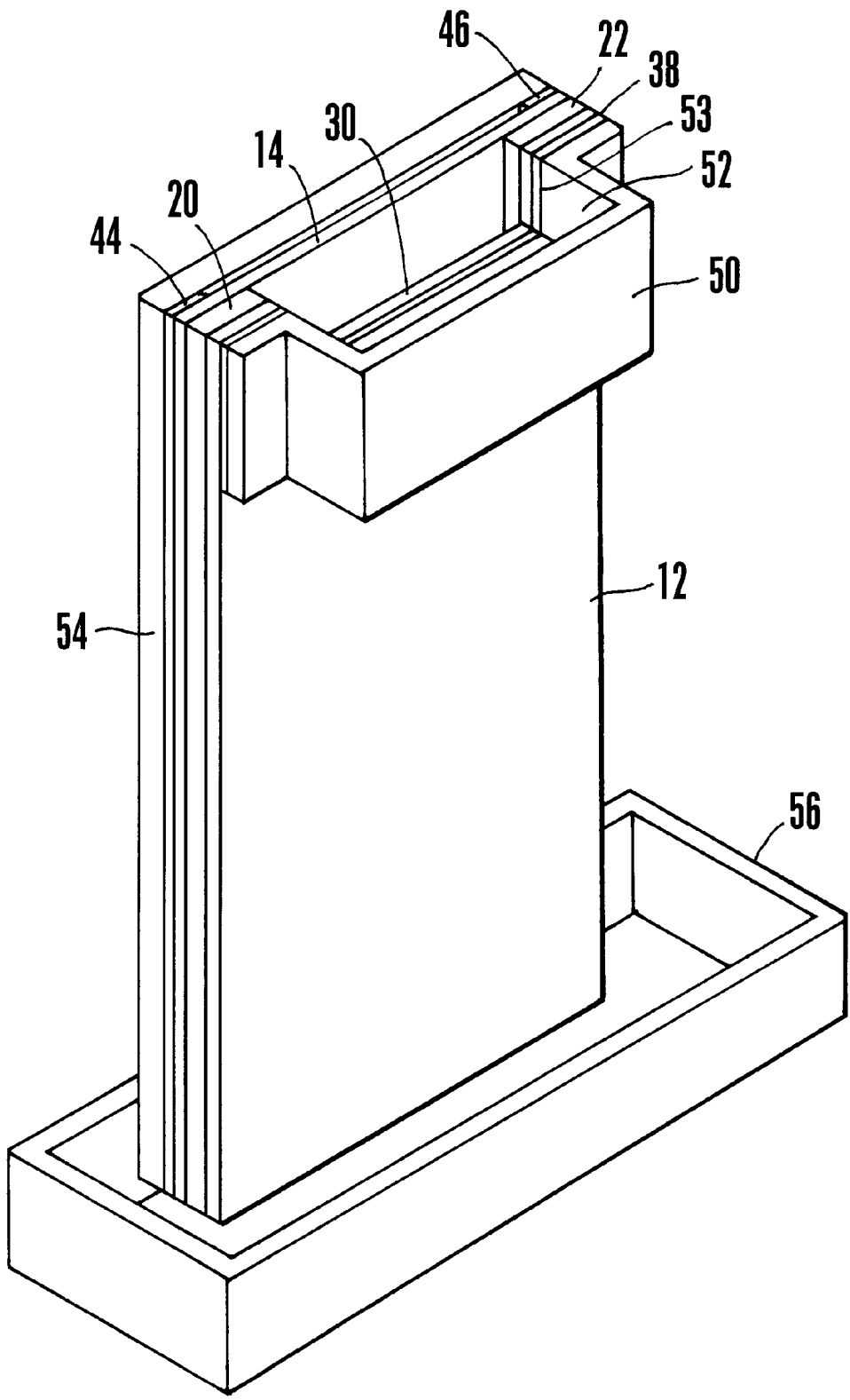
FIG. 4 is a perspective view of the first embodiment of the present cassette, showing the upper buffer tank and glass cover attached to the plastic plates of the cassette, schematically showing the cassette disposed in a lower buffer tank.

Referring initially to FIGS. 1—3, an electrophoresis gel cassette is shown, generally designated 10, which includes a parallelepiped-shaped first plate 12 and a parallelepiped-shaped second plate 14. If desired, the plates 12, 14 may be made of glass, but more preferably the plates 12, 14 are made of a resin film, such as polyester. Or, the plates 12, 14 can be made of polyvinylchloride (PVC) film.

As shown, the plates 12, 14 face each other and are closely spaced from each other, thus defining a gel chamber 16 (FIGS. 1 and 3) between the plates 12, 14. In accordance with the process described below, a gel 18 (FIGS. 2 and 3), preferably a polyacrylamide gel, is disposed in the gel chamber 16. To space the plates 12, 14 apart as shown, left and right plastic spacer strips 20, 22 are sandwiched between the plates 12, 14 along respective left and right sides 24, 26 of the cassette 10. The spacer strips 20, 22 can be made of PVC film.

As shown best in FIG. 1, the first plate 12 defines a top edge 28, and the first plate 12 can be formed with a cutout 30 in the top edge 28. In one preferred embodiment, the cutout 30 is defined by left and right vertical edges 32, 34 and a horizontal edge 36 therebetween.

A tank adhesive element 38 is attached to the first plate 12, and the adhesive element 38 borders the cutout 30. In other words, the tank adhesive element preferably conforms to the cutout 30. It is to be understood that the tank adhesive element 38 is configured for holding an upper buffer tank against the first plate 12 as more fully disclosed below. In the preferred embodiment, the tank adhesive element 38 is double backed tape, i.e., the adhesive element is tape having an adhesive cassette surface 40 that is pressed against the first plate 12 and an adhesive tank surface 42 that faces away from the first plate 12, as shown in cross-reference to FIGS. 1 and 2. It is to be understood that prior to use, the tank surface 42 can be covered by a non-adhesive protective sheet (not shown).

Left and right glass adhesive elements 44, 46 are attached to the second plate 14. In the preferred embodiment, the glass adhesive elements 44, 46 are strips of double backed tape that respectively extend the length of the left and right sides 24, 26 of the cassette 10 as shown. Accordingly, taking the left glass adhesive element 44 as an example, the left glass adhesive element 44 defines an adhesive glass engaging surface 48 that faces away from the plates 12, 14. As described in detail below, a glass support cover (not shown in FIGS. 1–3) is adhered to the glass engaging surfaces of the glass adhesive elements 44, 46.

To dispose the gel 18 between the plates 12, 14, the gel in a liquefied state is allowed to flow into the gel chamber 16, between the spacer strips 20, 22, and then allowed to polymerize. A comb (not shown) can be disposed in the gel during polymerization in accordance with gel casting principles known in the art. When the gel has polymerized and excess gel removed from surfaces of the cassette 10, the double backed adhesive elements 38, 44, 46 are applied to the plates 12, 14 as described above.

When it is desired to use the cassette 10 for electrophoretic DNA sequencing, as best shown in FIG. 4 a plastic upper buffer tank 50 is pressed against the tank surface 42 of the tank adhesive element 38, to adhere the tank 50 to the first plate 12. The upper buffer tank 50 can be made of acrylic or polycarbonate resin. As shown in FIG. 4, the upper buffer tank 50 defines a buffer chamber 52 for holding electrophoresis buffer solution therein. The buffer chamber is formed with an open side 53 that faces the first plate 12, and the buffer chamber 52 consequently communicates with the cutout 30 of the first plate 12 and, hence, with the gel 18 in the gel chamber 16.

Moreover, a glass support cover 54 is pressed against the glass adhesive elements 44, 46 to adhere the glass support cover 54 to the second plate 14 and thereby provide structural support to the plates 12, 14. As can be appreciated in reference to FIG. 4, the glass support cover 54 is the same size and configuration as the second plate 14. In accordance with present principles, the glass support cover 54 maintains the plates 12, 14 in a flat configuration to promote effective electrophoresis.

The cassette 10 is then disposed in a lower buffer tank 56. Both buffer tanks 50, 56 are then filled with electrolytic solution. Next, the DNA fragments to be analyzed, having been previously tagged with an appropriate tag such as a radioisotope, are deposited onto the gel 18. An electric field is then applied to the solutions in the buffer tanks 50, 56, such that the solution in the upper buffer tank 50 preferably is cathodic and the solution in the lower buffer tank 56 preferably is anodic.

After the DNA constituents have separated as a result of the ensuing electrophoresis, the cassette 10 is removed from the lower buffer tank 56, and the upper buffer tank 50 is removed from the first plate 12, for subsequent reuse of the tanks 50, 56. The cassette 10 is placed in an appropriate analysis device such as an x-ray reader to determine the DNA sequence from the pattern on the x-ray photograph.

It may now be appreciated that owing to the use of double backed tape as an adhesive element, the upper buffer chamber 50 does not require a groove for receiving a rubber gasket, consequently simplifying the construction and reducing the cost of the upper buffer chamber 50. It will be further appreciated that the plates 12, 14 of the cassette 10 can be made inexpensively and then disposed of after use, while permitting reuse of the buffer tanks 50, 56 and glass support cover 54.

Figure 5:
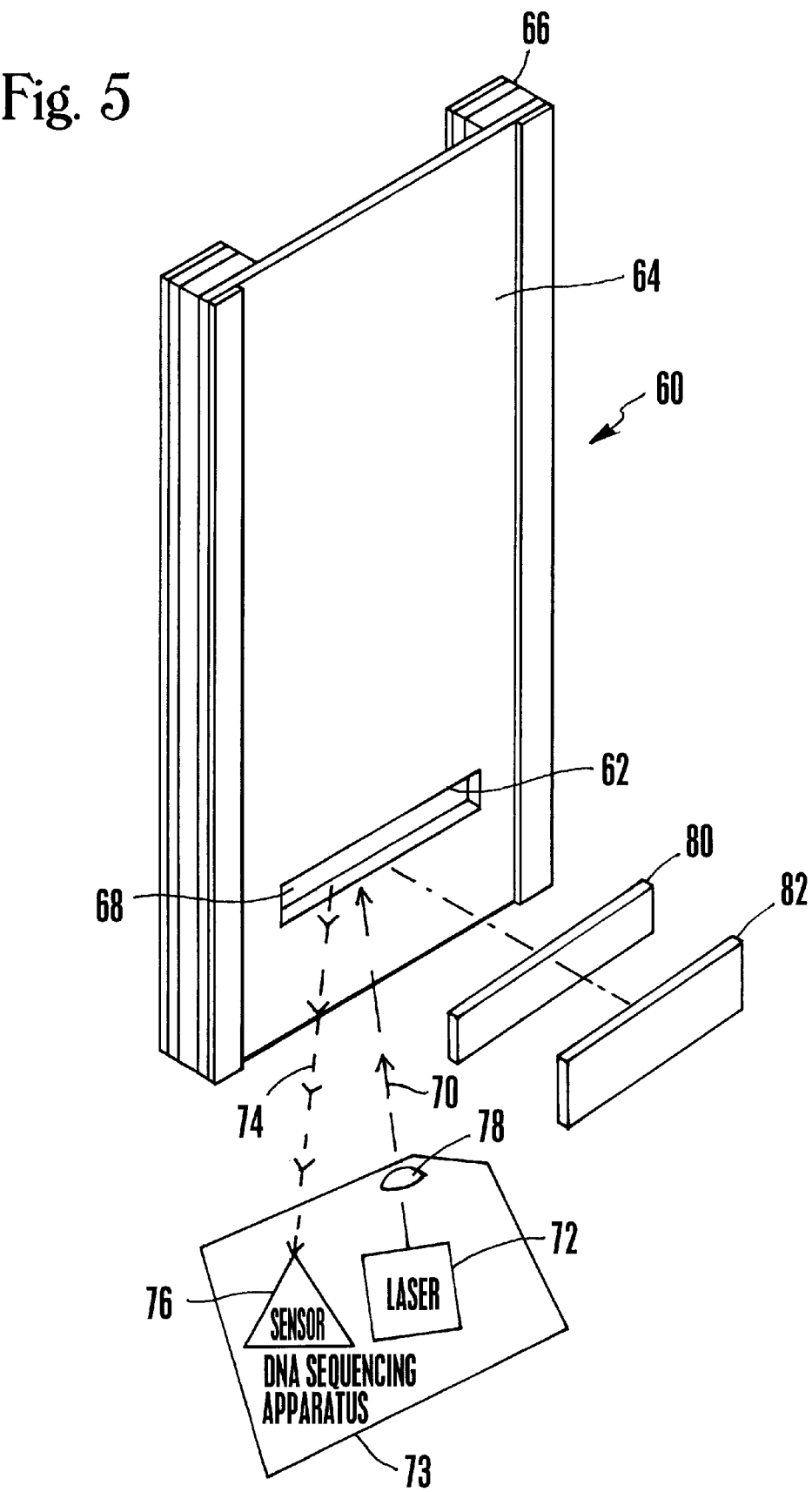
FIG. 5 is a perspective view of a second embodiment of the present cassette for automatic DNA sequencing, showing the passageway cover and cover tape in an exploded relationship with the cassette and schematically showing a laser with focussing lens directing a laser beam into the window to cause a fluorescent constituent in the gel to emit fluorescence.

FIG. 5 shows an alternate embodiment of the present invention including a cassette 60 that is in all essential respects identical to the cassette 10 shown in FIGS. 1–4, with the following exceptions. As discussed above, automatic DNA sequencing relies on directing a laser beam into a DNA-containing gel to cause fluorescent constituents in the DNA to emit fluorescence. The fluorescence is then detected and used to analyze the DNA.

With this in mind, to configure the cassette 60 to be suitable for automatic DNA sequencing, a window 62 is formed in a first plate 64 of the cassette 60. As shown, the window 62 can be rectangular, although other shapes can be used. Also, the window is shown formed in the first plate 64, but it is to be understood that the window 62 can alternatively be formed in a second plate 66 of the cassette 60.

In any case, it will be appreciated that the window 62 defines a light passageway 68 through which a laser beam 70 from a laser apparatus 72 of a DNA apparatus 73 can enter the cassette 60, and through which fluorescence 74 from the DNA inside the cassette can propagate back out of the cassette 60 for detection of the fluorescence by a sensor 76. If desired, the laser beam 70 can be focussed by a focussing lens 78. Per the present invention, the window 62 reduces or indeed eliminates interference, absorption, and reflection of relatively weak fluorescence that would otherwise occur if the fluorescence 74 from the DNA would have to propagate through a plastic object, such as the first plate 64, before arriving at a detection sensor.

A paper or plastic passageway cover 80 can be placed over the window 62 and held in place by a waterproof cover tape 82 that overlaps the cover 80 and window 62. The cover protects and covers the window 62 prior to use. Before the cassette is used for electrophoresis, the cover tape 82 and passageway cover 80 are removed from the cassette 10.

While the particular GEL CASSETTE FOR ELECTROPHORESIS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more".

What is claimed is:

1. A cassette for electrophoresis, comprising:

a first plate;

a second plate facing the first plate, a gel chamber being established between the plates;

at least a first adhesive element adhesively attached to the first plate, the first adhesive element defining an adhesive tank surface facing away from the plates for engaging an upper buffer tank when the upper buffer tank is pressed against the adhesive element; and at least a second adhesive element attached to one of: the first plate or second plate, the second adhesive element defining an adhesive engaging surface facing away from the plates for holding a support cover against the second adhesive element.

2. The cassette of claim 1, wherein the upper buffer tank defines a buffer chamber and the adhesive element is attached to the first plate, the first plate being formed with a cutout, the adhesive element bordering the cutout for holding the upper buffer tank against the first plate with the buffer chamber of the upper buffer tank in communication with the cutout.

3. The cassette of claim 2, wherein the plates are made of plastic and the cassette further comprises a gel disposed between the plates.

4. The cassette of claim 3, further comprising an upper buffer tank engaged with the adhesive tank surface.

5. The cassette of claim 1, further comprising a support cover engaged with the second adhesive surface.

6. The cassette of claim 1, wherein the gel chamber can hold at least a fluorescent constituent and the first plate is formed with a light passageway to permit light to propagate therethrough into the gel chamber and thereby cause the fluorescent constituent to emit fluorescence.

7. The cassette of claim 6, further comprising a passageway cover for selectively blocking the light passageway.

8. A cassette for electrophoresis, comprising:

a first plate;

a second plate facing the first plate, a gel chamber being established between the plates, the gel chamber being configured for holding a gel having at least a fluorescent constituent, at least the first plate or second plate being formed with a light passageway to permit light to propagate therethrough into the gel chamber and thereby cause the fluorescent constituent to emit fluorescence when the gel is disposed in the chamber; and a passageway cover for selectively blocking the light passageway.

9. The cassette of claim 8, further comprising a passageway cover for selectively blocking the light passageway.

10. The cassette of claim 8, wherein the plates are made of plastic and the cassette further comprises at least one adhesive element adhesively attached to one of the plates, the adhesive element defining an adhesive tank surface facing away from the plates for engaging an upper buffer tank when the upper buffer tank is pressed against the adhesive element.

11. The cassette of claim 10, wherein the upper buffer tank defines a buffer chamber and the adhesive element is attached to the first plate, the first plate being formed with a cutout, the adhesive element bordering the cutout for holding the upper buffer tank against the first plate with the buffer chamber of the upper buffer tank in communication with the cutout.

12. The cassette of claim 11, further comprising a gel disposed between the plates.

13. The cassette of claim 12, further comprising the upper buffer tank.

14. The cassette of claim 12, further comprising a glass adhesive element attached to the second plate, the glass adhesive element defining an adhesive glass engaging surface facing away from the plates for holding a glass support cover in juxtaposition with the second plate.

15. The cassette of claim 14, further comprising the glass support cover engaged with the glass adhesive surface.

16. A method assembling and using a gel cassette comprising the steps of:

holding a gel between two plastic plates;

attaching an upper buffer tank defining a buffer chamber to one of the plates using an adhesive tape having first and second adhesive sides;

attaching a cover to one of the plates; and disposing the plates in an electrophoresis apparatus for undertaking DNA sequencing.

17. The method of claim 16, further comprising the steps of:

forming a light passageway in one of the plates; and directing a beam of light through the light passageway into the gel to cause one or more fluorescent constituents in the gel to emit fluorescence.

18. The method of claim 17, further comprising the step of selectively covering the light passageway.

* * * * *